United States Patent [19]
Flower et al.

[11] Patent Number: 6,029,083
[45] Date of Patent: Feb. 22, 2000

[54] CIRCUIT AND METHOD FOR AUTOMATICALLY TURNING OFF AN IONTOPHORESIS SYSTEM

[75] Inventors: Ronald J. Flower, Vernon, N.J.; Kenneth E. Garde, New Windsor, N.Y.

[73] Assignee: Becton, Dickinson and Company, Franklin Lakes, N.J.

[21] Appl. No.: 08/835,085

[22] Filed: Apr. 4, 1997

[51] Int. Cl.[7] .................................................. A61N 1/30
[52] U.S. Cl. ............................................... 604/20; 607/59
[58] Field of Search ............... 604/20–21; 607/149–153, 607/59

[56] References Cited

U.S. PATENT DOCUMENTS

| | | |
|---|---|---|
| 4,141,359 | 2/1979 | Jacobsen et al. . |
| 5,645,526 | 7/1997 | Flower . |
| 5,697,896 | 12/1997 | McNichols et al. . |

*Primary Examiner*—Mark Bockelman
*Attorney, Agent, or Firm*—Arthur D. Dawson

[57] ABSTRACT

A fail-safe iontophoretic drug delivery apparatus and a corresponding method is provided. The apparatus includes a current generating circuit for sending a current through a patch, error detection circuitry, and a control circuit. The control circuit controls the current generating circuit. When errors are detected in the apparatus, the control circuit stops the current and disables itself.

24 Claims, 8 Drawing Sheets

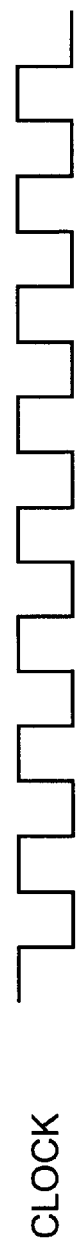
FIG-5a  CLOCK
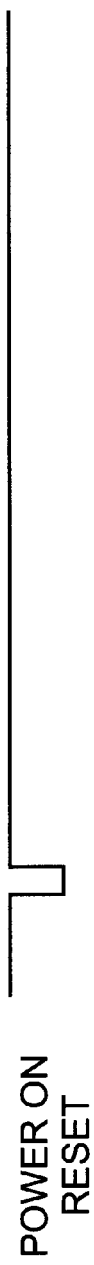
FIG-5b  POWER ON RESET

DATA STORE OUT Q

μp clk IN

6,029,083

CIRCUIT AND METHOD FOR AUTOMATICALLY TURNING OFF AN IONTOPHORESIS SYSTEM

BACKGROUND OF THE INVENTION

1. Field of the Invention

The invention is in the field of iontophoresis. In particular, the invention relates to irrevocably shutting down an electronic controller of an iontophoretic delivery device when certain error conditions are detected, thereby preventing unintentional delivery of drugs.

2. Description of Related Art

Iontophoresis is the application of an electrical current to transport ions through intact skin. One particularly advantageous application of iontophoresis is the non-invasive transdermal delivery of ionized drugs or other therapeutic agents into a patient. This is done by applying low levels of current to a patch placed on the patient's skin, which forces the ionized drugs contained in the patch through the patient's skin and into his or her bloodstream.

Passive transdermal patches, such as those used to deliver nitroglycerin for angina pectoris, estradiol for hormone replacement, and nicotine to stop smoking, can only use a limited number of drugs because they work by diffusion. Iontophoresis advantageously expands the range of drugs available for transdermal delivery, including, for example, parenteral drugs (e.g., peptides). Further, because the amount of drug delivered is related to the amount of current applied, the drug delivery rate can be precisely controlled by controlling the current, unlike the passive transdermal patches. This allows for more rapid delivery (onset) and drug reduction (offset) in the patient.

When compared to drug delivery by needle injection, iontophoresis can have less physical and emotional trauma, pain, and possibility of infection. Transdermal drug delivery by iontophoresis also avoids the risks and inconvenience of IV (intravenous) delivery. In addition, when compared to oral ingestion of drugs, drug delivery by iontophoresis bypasses the GI tract, thus reducing side-effects such as drug loss, indigestion and stomach distress, and eliminating the need for swallowing the drug. Iontophoresis also avoids drug loss due to hepatic first pass metabolism by the liver that occurs when drugs are ingested.

Further, transdermal drug delivery by iontophoresis permits continuous delivery of drugs with a short half life and easy termination of drug delivery. Because iontophoresis is more convenient, there is a greater likelihood of patient compliance in taking the drug. Thus, for all of the above reasons, iontophoresis offers an alternative and effective method of drug delivery, and an especially useful method for children, the bedridden and the elderly.

An iontophoretic drug delivery system typically includes a current source, such as a battery and current controller, and a patch. The patch includes an active reservoir and a return reservoir. The active reservoir contains the ionized drug, in, for example, a conductive gel. The return reservoir contains a saline gel and collects ions emanating from the patient's skin when the drug is being delivered into the patient's skin.

The patch also has two electrodes, each arranged inside the active and return reservoirs to be in respective contact with the drug and saline. The anode, or positive, electrode and the cathode, or negative, electrode are respectively electrically connected to the anode and cathode of the current source by electrical conductors. Either the anode electrode or the cathode electrode is placed within the drug reservoir, depending on the charge of the ionized drug. This electrode is designated as the active electrode. The other electrode is placed within the return reservoir, and is designated as the return electrode.

The active electrode has the same charge as the ionized drug to be delivered and the return electrode has a charge opposite of the drug to be delivered. For example, if the drug to be delivered to the patient has a positive ionic charge, then the anode will be the active electrode and the cathode will be the return electrode. Alternatively, if the drug to be delivered has a negative ionic charge, then the active electrode will be the cathode and the return electrode will be the anode. When current from the current source is supplied to the active electrode, the drug ions migrate from the drug gel in the reservoir toward and through the skin of a patient. At the Same time, oppositely-charged ions flow from the patient's skin into the saline solution of the return reservoir. Charge is transferred into the return electrode and back to the current source, completing the iontophoretic circuit.

The electronic controller between the battery and the electrodes delivers the required current to the patch. The controller may control the output current so that drug delivery is accomplished at a constant or varying rate, or over a short, long or periodic time interval. These controllers generally require relatively complex electrical circuits, sometimes including microprocessors, to meet the above requirements.

While the circuits used for iontophoretic are very reliable, error conditions, including malfunctions in the electronic controller, can nevertheless occur. If these error conditions are not corrected, an incorrect drug dosage could be delivered to a patient.

Accordingly, a desirable safety feature for an iontophoretic system is to irrevocably shut down the electronic controller when certain error conditions are detected. These error conditions include misuse of the iontophoretic system (which could be either intentional or by accident), as well as failures in the controller circuitry or, if applicable, controller software.

SUMMARY OF THE INVENTION

It is an object of the invention to provide a controller which irrevocably shuts off the iontophoretic current when misuse of the iontophoretic system is detected or system errors occur.

In one aspect of the invention, a controller for an iontophoretic drug delivery apparatus is provided. This controller includes a current generating circuit, error detection circuitry, and a control circuit capable of controlling the current generating circuit. The control circuit disables itself when the error detection circuitry detects an error condition. A preferred approach to disabling the control circuit is by stopping the control circuit's clock signal.

In another aspect of the invention, a method of shutting down an iontophoretic drug delivery system is provided. This method includes the steps of controlling an iontophoretic current using a control circuit capable of being disabled, detecting an error condition, and disabling the control circuit after the error condition is detected.

BRIEF DESCRIPTION OF THE DRAWINGS

These and other objects, features and advantages of the present invention can best be understood by reference to the detailed description of the preferred embodiments set forth below taken with the drawings, in which:

FIGS. 5a–5f depict waveforms of the various circuit states of the first embodiment.

DETAILED DESCRIPTION OF THE PREFERRED EMBODIMENTS

Figure 1:
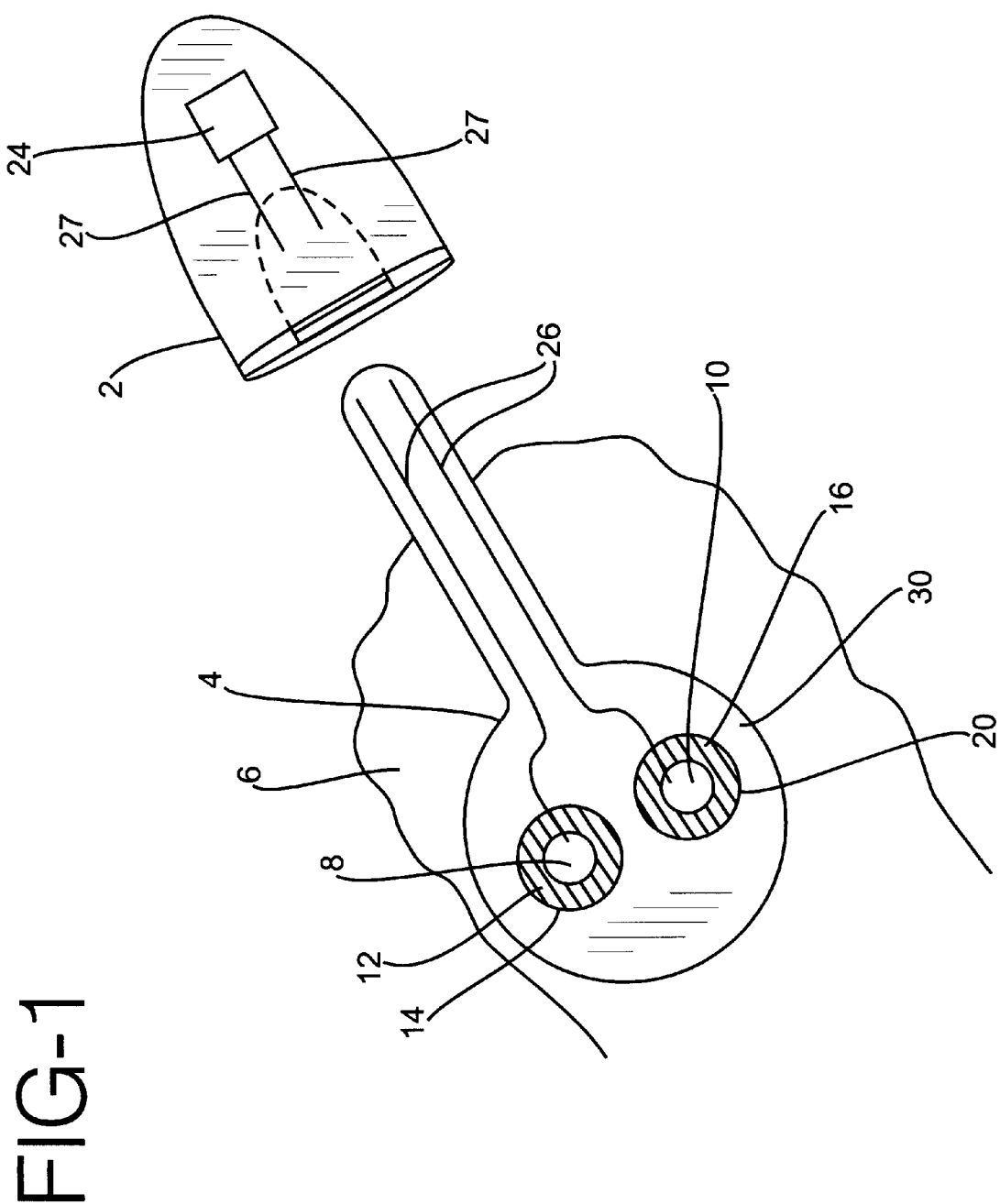
FIG. 1 is a perspective view of an iontophoretic drug delivery device.

One type of iontophoretic drug delivery device includes a separate, reusable controller 2, which can be removably and electrically connected to a patch 4 containing the drug, therapeutic agent or medicament, as shown in FIG. 1. The patch 4 is attached to the skin of the patient 6. The patch includes an active electrode 8 and a return electrode 10, with the ionic drug 12 and active electrode 8 positioned within the active reservoir 14, and the saline or electrolyte 16 and return electrode 10 positioned within the return reservoir 20.

Figure 2:
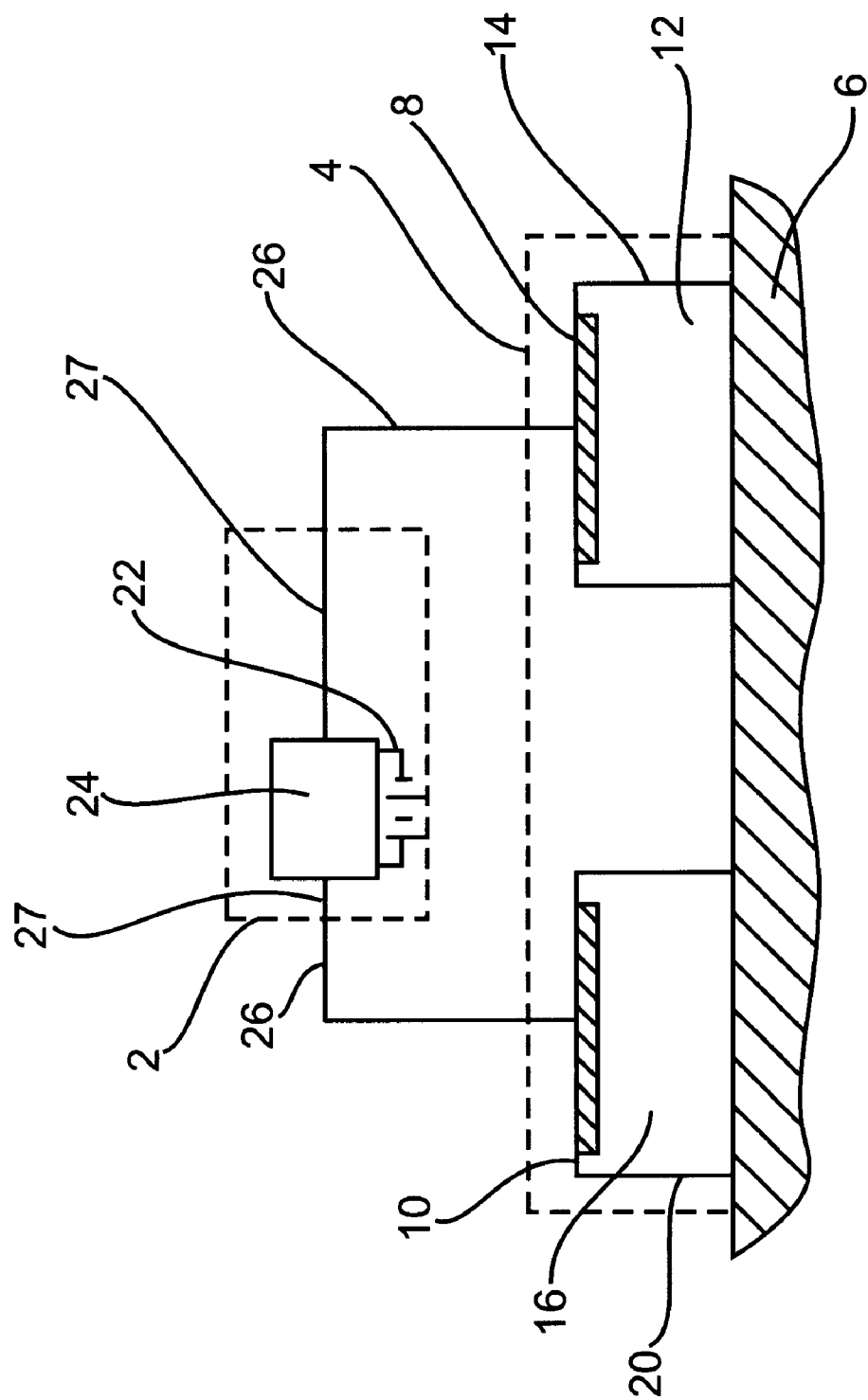
FIG. 2 is a high-level block diagram of an iontophoretic drug delivery device.

The iontophoretic drug delivery device also includes a controller 2 having a power supply 22 and electronic control circuitry 24, as shown in FIG. 2. The controller is electrically coupled to the patch 4 using electronic interconnectors 26, such as a printed flexible circuit, metal foils, wires, tabs or electrically conductive adhesives. The power supply 22 in combination with the electrodes 8 and 10 and the patient's body 6 completes the circuit and generates an electric field across the body surface or skin on which the iontophoretic device is applied. The electric field causes the drug in the active reservoir 14 to be delivered into the body of the patient by iontophoresis.

Patch 4 is generally a planar flexible member formed of, for example, a biocompatible material such as woven or non-woven textiles or polymers, or any other construction well-known in the art. The patch is attached to the patient's skin using adhesives or a strap or both. The patch includes an enlarged patch body 30, which includes the active and return reservoirs.

The lower surface of the reservoirs are placed in contact with the skin. The electrodes are positioned so that an electrical current path is established between the electrodes 8 and 10 through the reservoirs and the patient's skin 6. Electrodes 8 and 10 are placed in conductive contact with the reservoirs 12 and 16, respectively. A direct current source may be connected to the electrodes 8 and 10 so that the active electrode has the same charge polarity as the ionic drug 12. When current is passed through the active electrode 8 to the return electrode 10 through the skin 6, the ionic drug 12 contained in the active reservoir 14 is delivered through the skin 6 and into the patient.

Figure 3:
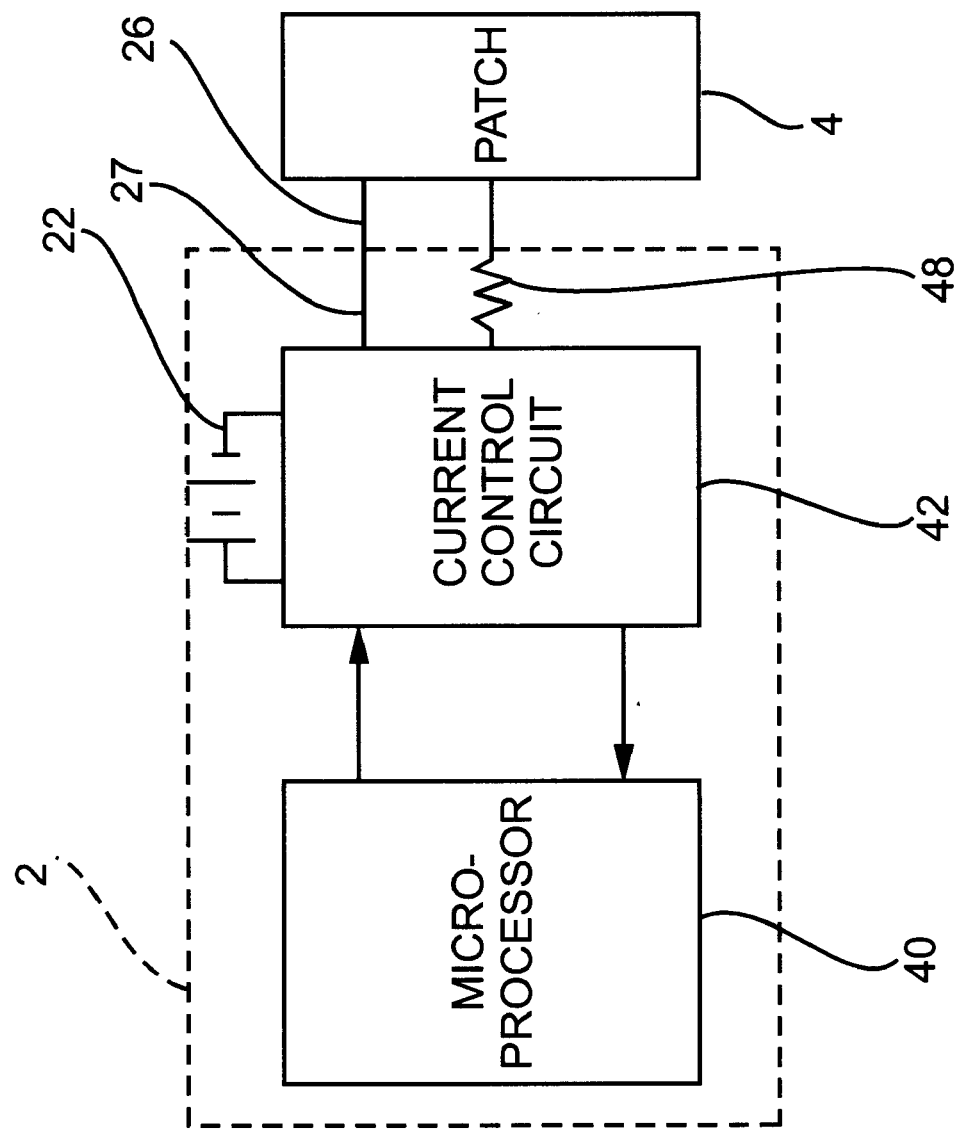
FIG. 3 is a block diagram of a iontophoretic controller circuit.

The controller 2 may include, but is not limited to, battery 22, microprocessor 40, and current control circuit 42, as shown in FIG. 3. The microprocessor 40 provides signals to the current control circuit 42 to ensure that the required current is delivered by the current control circuit 42 to the connected patch through conductors 27 and 26 to electrodes 8 and 10 (shown in FIG. 2) so that the correct amount of drug is delivered to the patient. The current control circuit 42 will produce from the battery 22 the required output current irrespective of the varying resistance and/or capacitance of the load (including the patient's skin, the impedance of which normally varies from patient to patient and which may change as iontophoresis takes place).

Further, voltage from a sensor, such as a current sense resistor 48, is monitored by the current control circuit 42 to ensure that the amount of delivered current is constant. The current passing through the current sense resistor 48 is the amount of current actually being delivered through the iontophoretic patch and skin. If less or more than the required current is being delivered, as indicated by the current sense resistor 48, the current control circuit 42 will adjust the current to the required level.

In order to increase the safety of the iontophoretic drug delivery system, it would be advantageous to irrevocably shut down and disable the iontophoretic controller when certain error conditions occur, thereby stopping the delivery of the drug.

Examples of conditions which may be used to trigger this irrevocable shut down might include, for example, the patch being removed from the controller. This would ensure that a particular controller can be used only once. Another condition could be when an incorrect or expired patch is plugged in to the controller. Other conditions include self-test failures such as low battery voltage, reference voltage failure, clock failure, current generating circuit overvoltage, current generating circuit overcurrent, and current generating circuit time-current product exceeded.

Figure 4:
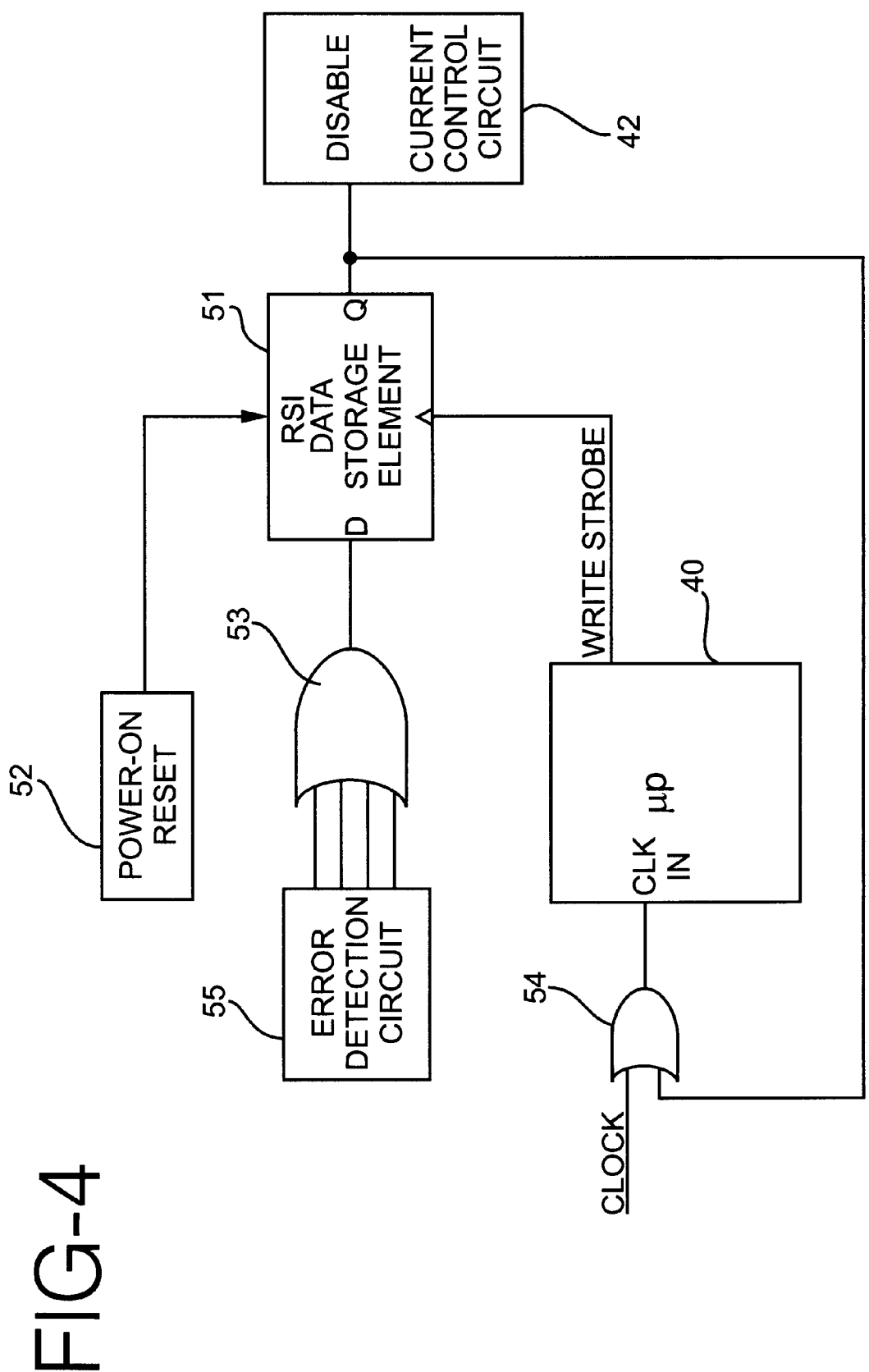
FIG. 4 is a block diagram of an automatic shut-off feature for an iontophoretic controller circuit, in accordance with a first embodiment of the present invention.

FIG. 4 is a block diagram representation of a first embodiment of the present invention that implements an automatic, irrevocable shutdown function in an iontophoretic controller. The waveforms shown in FIGS. 5a–5f depict the operation of the circuit of FIG. 4. Accordingly, the first embodiment will be described by referring to FIG. 4 and FIGS. 5a–5f together.

The circuit includes a microprocessor 40 which executes program instructions stored in a memory (not shown). The microprocessor, however, can only execute the program instructions when a clock signal is applied to the microprocessor's clock input. Storage element 51 is used to store a bit of data. This storage element may be a flip-flop, register, latch, RAM, EEPROM, or the like. When the power is turned on for the first time, a power-on reset circuit 52 generates a power-on reset pulse (FIG. 5b) which resets the storage element 51 by storing a ZERO in it, thereby driving the output Q (FIG. 5e) of the data storage element 51 low.

After the power is turned on, and during ordinary operation of the system, the output Q (FIG. 5e) of the storage element 51 is low. As a result, OR gate 54 will pass the clock signal (FIG. 5a) that is present at the upper input of the OR gate 54 to the microprocessor clock input (FIG. 5f), thereby enabling the microprocessor 40 to execute program instructions.

Figure 5C:
Figure 5D:
Figure 5E:
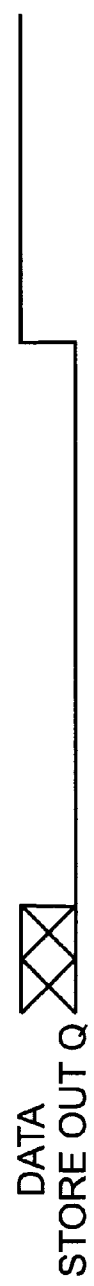
Figure 5F:
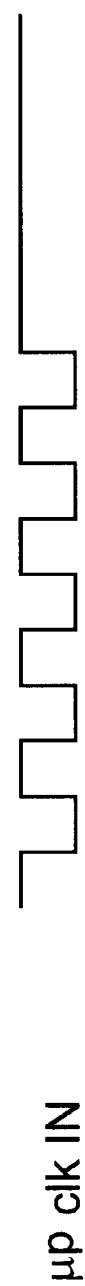

The microprocessor also has a write strobe output (FIG. 5d). The circuitry required to generate this write strobe output may be included in the microprocessor itself, as depicted in FIG. 4. Alternatively, it may be implemented in control logic that is external to the microprocessor 40. Generation of write strobes is well known in the art of microprocessor based electronic circuit design. When the microprocessor 40 generates a write strobe, the data present at the D input of the storage element 51 is stored, and the stored data also appears at the output of the storage element 51.

Error detection circuit 55 has a number of outputs, each corresponding to a particular error condition. In this embodiment, when any of the error conditions is present, the corresponding output of the error detection circuit is high. When a given error is not present, the corresponding output is low. Although not shown in this figure, the microprocessor may be able to read the status of the error detection circuit outputs.

OR gate 53 combines the outputs of the error detection circuit 55 into a composite error signal (FIG. 5c). Because of the logical OR function performed in the OR gate, the output of the OR gate will be high when any one of the error conditions is detected by the error detection circuit 55. The composite error signal (FIG. 5c) at the output of OR gate 53 will only be low when no error conditions are detected by the error detection circuit 55.

If the microprocessor generates a write strobe (FIG. 5d) when the composite error signal (FIG. 5c) at the output of OR gate 53 is low, the output Q (FIG. 5e) of the data storage element 51 remains low. As a result, OR gate 54 will continue to pass the clock signal (FIG. 5a) that is present at the upper input of the OR gate 54 to the microprocessor clock input (FIG. 5f), and the microprocessor will continue to execute its program.

If, however, the microprocessor generates a write strobe (FIG. 5d) when the composite error signal (FIG. 5c) is high, the write strobe causes a ONE to be written into the storage element. When a ONE is written into the storage element, the output of the OR gate 54 that is applied to the microprocessor clock input (FIG. 5f) goes high, and it will remain high no matter what happens to the clock signal (FIG. 5a) at the upper input of OR gate 54. This stops the clock signal (FIG. 5f) at the microprocessor clock input. When the clock signal (FIG. 5f) to the microprocessor 40 is stopped, the microprocessor 40 cannot execute any more instructions, as explained above. Thus, by generating a write strobe ( FIG. 5d) when an error condition exists, the microprocessor 40 prevents itself from executing further instructions.

When the output Q (FIG. 5e) of the data storage element 51 is high, the current control circuit 42 should be disabled so that it does not generate current. This can be accomplished by a logic-level disable input, as shown in FIG. 4. Alternatively, a signal downstream from the output Q (FIG. 5e) of the storage element 51, such as the output of the OR gate 54 (FIG. 5f), may be used to disable the current control circuit 42. As yet another alterative, a second data storage element output (not shown) may be used to disable the current source, provided that the appropriate disabling data is written to the second data storage element before the microprocessor 40 shuts itself off.

Because the microprocessor 40 cannot execute instructions when the clock signal is stopped, the microprocessor 40 cannot generate an additional write strobe, or initiate any other action, to clear the storage element. Accordingly, this stopped condition is permanent, unless the system is restarted as explained below. It should be noted that, because the microprocessor 40 cannot execute any instructions after shutting itself off, the microprocessor 40 should preferably be programmed to put the controller into a safe state before shutting itself off.

In this embodiment, the only way to restart the system is to remove power from the system completely (for example, by removing the batteries). Then, when power is ultimately reapplied, the power-on reset circuit 52 will return the storage element 51 to its initial ZERO state, as described above, and the clock signal (FIG. 5a) will be able to pass through the OR gate 54 and reach the clock input (FIG. 5f) of the microprocessor 40.

Of course, many alternative embodiments to the circuit described above can be readily envisioned. For example, in the embodiment depicted in FIG. 6, the output bits from the error detection circuit 55 are read into the microprocessor 40, and those bits are ORed together by the microprocessor into a single bit. This single bit is then written, by the microprocessor, into the storage element 51 via the data bus which is connected to the D input of the storage element 51. Alternatively, the output of the data storage element 51 may be set by a dedicated strobe connected to a set input of the storage element 51. As yet another alternative, the microprocessor based design may be replaced by a different type of control circuit, such as a logic-based state machine (not shown).

If desired, a circuit that can never be restarted, even when power is removed, can be implemented by using, for example, a fuse programmable device like a PROM (programmable ROM), a PAL (programmable array logic), or the like. These devices are programmed by blowing a physical fuse that can never be restored. Of course, when these devices are used, the necessary programming circuitry must also be included.

As an alternative to disabling the control circuit by stopping a clock signal, numerous other approaches may be used. Some examples include asserting a reset line to a microprocessor and removing battery power from the apparatus. Numerous other examples can be readily envisioned.

Figure 6:
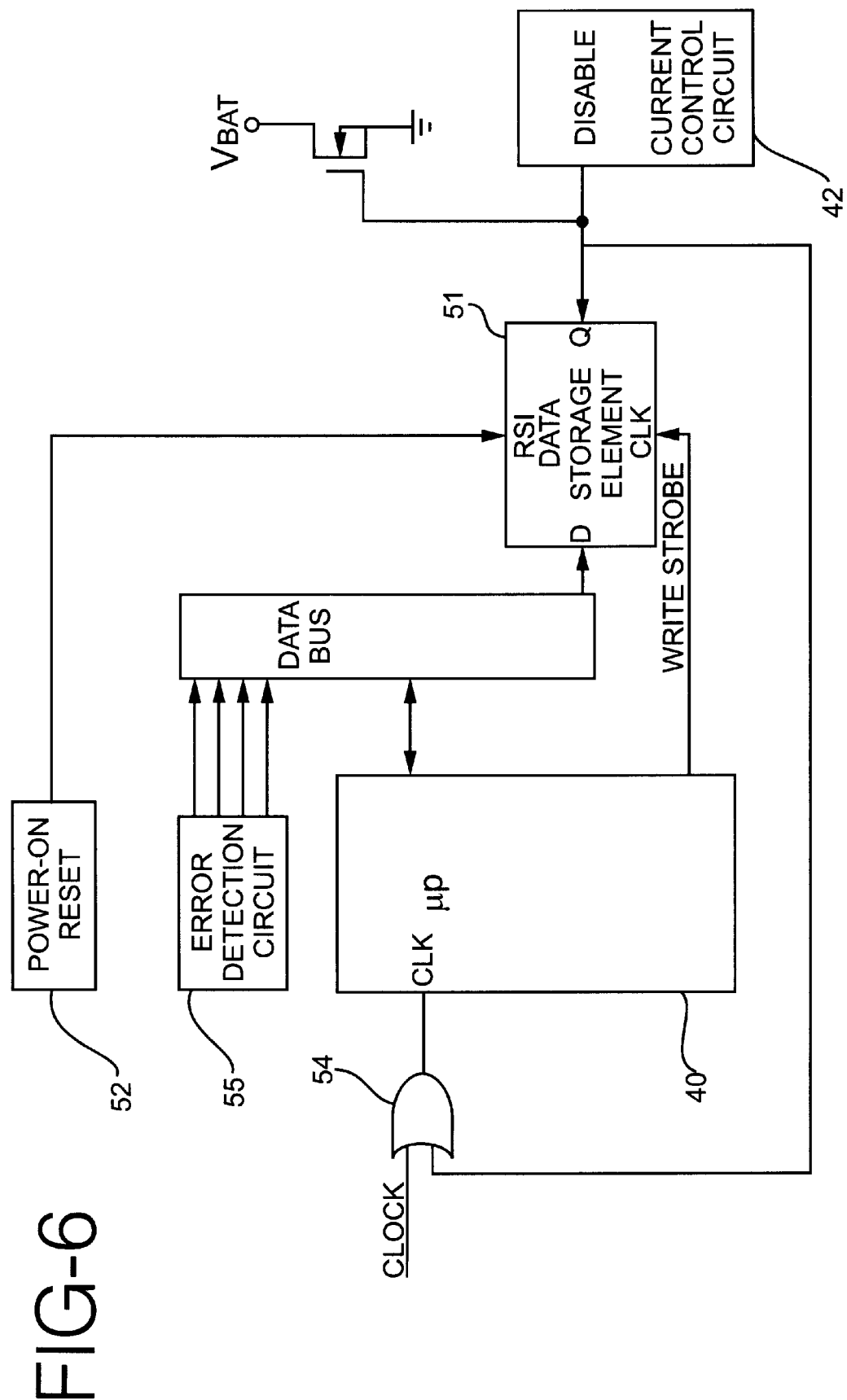
FIG. 6 is a block diagram of an automatic shut-off feature for an iontophoretic controller circuit, in accordance with a second embodiment of the present invention.

A battery draining circuit, such as the field effect transistor (FET) 56 shown in FIG. 6 or a silicon controlled rectifier (SCR) or a bipolar transistor (not shown), may optionally be included to drain the battery when the microprocessor 40 is shut down. This can provide an extra measure of safety by disabling the controller in an additional way.

Of course, it will be appreciated that the invention may take forms other than those specifically described, and the scope of the invention is to be determined solely by the following claims.

What is claimed is:

1. A controller for an iontophoretic drug delivery apparatus, comprising:

a current control circuit;

error detection circuitry for detecting at least one error condition within the apparatus; and a control circuit including a microprocessor capable of controlling said current control circuit, said control circuit being capable of disabling itself from reading instruction when said error detection circuitry detects the at least one error condition, said controller further comprising power-on reset circuitry to ensure that said control circuit is not disabled when power is initially applied.

2. The apparatus according to claim 1, further comprising a battery draining circuit that is activated when the control circuit is disabled.

3. The apparatus according to claim 1, wherein the error detection circuitry detects at least one of the conditions of low battery voltage, reference voltage failure, clock failure, current generating circuit overvoltage, current generating circuit overcurrent, excess time-current product, expired patch installed, and incorrect patch installed.

4. The apparatus according to claim 1, further comprising an iontophoretic patch, said patch being electrically connectable to said current generating circuit, said patch for delivering drugs to the patient when said current generating circuit is in an operational state.

5. A controller for an iontophoretic drug delivery apparatus, comprising:

a current control circuit;

means for providing a clock signal;

error detection circuitry for detecting at least one error condition within the apparatus; and a control circuit capable of controlling said current control circuit, said control circuit having a clock input, said control circuit being capable of operating only when a clock signal is applied to the clock input, said control circuit being further capable of stopping the clock signal applied to the clock input when said error detection circuitry detects the at least one error condition.

6. The apparatus according to claim 5, wherein said current generating circuit is shut off when the clock signal is stopped.

7. The apparatus according to claim 6, further comprising power-on reset circuitry to ensure that the clock signal is on when power is initially applied.

8. The apparatus according to claim 6, wherein the control circuit comprises a microprocessor.

9. The apparatus according to claim 6, further comprising a battery draining circuit that is activated when the clock signal is stopped.

10. The apparatus according to claim 9, wherein the battery draining circuit comprises at least one of an SCR, a bipolar transistor, and an FET.

11. The apparatus according to claim 6, wherein the error detection circuitry detects at least one of the conditions of low battery voltage, reference voltage failure, clock failure, current generating circuit overvoltage, current generating circuit overcurrent, excess time-current product, expired patch installed, and incorrect patch installed.

12. The apparatus according to claim 6, further comprising an iontophoretic patch, said patch being electrically connectable to said current generating circuit, said patch for delivering drugs to the patient when said current generating circuit is in an operational state.

13. A controller for an iontophoretic drug delivery apparatus, comprising:

a current control circuit;

means for providing a clock signal;

a data storage device having an output, wherein the output is in a first state when certain data is stored in said data storage device, and is not in the first state when the certain data is not stored in said data storage device;

a control circuit capable of controlling said current generating circuit and capable of causing the certain data to be stored into said data storage device, said control circuit having a clock input, said control circuit being capable of operating only when a clock signal is applied to the clock input;

a logic circuit having an output connected to the clock input of the control circuit, a control input connected to the output of the data storage device, and a clock input adapted to receive a first clock signal, wherein a second clock signal is produced at the logic circuit output only when the data storage device output is not in the first state;

error detection circuitry for detecting at least one error condition within the system; and power-on reset circuitry to ensure that the certain data is not stored in said data storage device when power is initially applied, wherein said control circuit causes the certain data to be stored in said data storage device when said error detection circuitry detects the at least one error condition, and wherein said current generating circuit is shut off when the certain data is stored in said data storage device.

14. The apparatus according to claim 13, wherein said control circuit comprises a microprocessor.

15. The apparatus according to claim 13, further comprising a battery draining circuit that is activated when the certain data is stored in said data storage device.

16. The apparatus according to claim 15, wherein the battery draining circuit comprises at least one of an SCR, a bipolar transistor, and an FET.

17. The apparatus according to claim 13, wherein the error detection circuitry detects at least one of the conditions of low battery voltage, reference voltage failure, clock failure, current generating circuit overvoltage, current generating circuit overcurrent, excess time-current product, expired patch installed, and incorrect patch installed.

18. The apparatus according to claim 13, wherein the data storage device comprises one of a group consisting of a register, latch, RAM, PROM, EPROM, EEPROM, and fuse programmable device.

19. The apparatus according to claim 13, further comprising an iontophoretic patch, said patch being electrically connectable to said current generating circuit, said patch for delivering drugs to the patient when said current generating circuit is in an operational state.

20. A method of shutting down an iontophoretic drug delivery system, comprising the steps of:

providing a clock signal;

controlling an iontophoretic current using a control circuit having a clock input, the control circuit being capable of operating only when a clock signal is applied to the clock input;

detecting at least one error condition within the system; and generating a signal by the control circuit that stops the clock signal from being delivered to the clock output after the at least one error condition is detected in said detecting step.

21. The method according to claim 20, further comprising the step of stopping the iontophoretic current when the clock signal is stopped.

22. The method according to claim 20, further comprising the step of starting the clock signal when power is initially applied.

23. A method of shutting down an iontophoretic drug delivery system, comprising the steps of:

controlling an iontophoretic current using a control circuit including a microprocessor capable of being disabled;

detecting at least one error condition within the system; and disabling the ability of the control circuit microprocessor from reading instructions after the at least one error condition is detected in said detecting step.

24. The method according to claim 23, further comprising the step of stopping the iontophoretic current when the control circuit is disabled.

* * * * *